(12) United States Patent
Flanigan et al.

(10) Patent No.: US 6,798,220 B1
(45) Date of Patent: Sep. 28, 2004

(54) MOISTURE/MOLD DETECTOR

(75) Inventors: Timothy H. Flanigan, 1919 Cenacle La., Carmichael, CA (US) 95608; John C. Flanigan, Granite Bay, CA (US); Alexander Finogenov, El Dorado Hills, CA (US)

(73) Assignee: Timothy H. Flanigan, Carmichael, CA (US)

( * ) Notice: Subject to any disclaimer, the term of this patent is extended or adjusted under 35 U.S.C. 154(b) by 48 days.

(21) Appl. No.: 10/180,840

(22) Filed: Jun. 24, 2002

Related U.S. Application Data
(60) Provisional application No. 60/301,538, filed on Jun. 27, 2001.

(51) Int. Cl.[7] .............................................. G01R 27/08
(52) U.S. Cl. ...................................... 324/696; 340/604
(58) Field of Search .......................... 340/604; 324/696

(56) References Cited

U.S. PATENT DOCUMENTS

| | | | |
|---|---|---|---|
| 6,052,066 A | * | 4/2000 | Su ......................... 340/870.16 |
| 2002/0130781 A1 | * | 9/2002 | Kroll et al. .................. 340/604 |

FOREIGN PATENT DOCUMENTS

| | | | | |
|---|---|---|---|---|
| GB | 2256926 A | * | 12/1992 | .......... G01N/27/04 |

OTHER PUBLICATIONS

"Moisture Meters and Electro Magnetic Field Testers for Industrial Hygienists", http://www.afcintl.com/ih1.htm.
Protimeter Brochure—http://www.moisture–meter.com.
"Moisture Encounter", TRAMEX Moisture Detection Equipment http://www.tramexltd.com/page/moist.html.
TRAMEX Survey Encounter Intelligent Moisture Meter http://www.yestek.com/tramex_se.htm.
"Wet Wall Detector" TRAMEX Moisture Detection Equipment http://www.tramexltd.com/page/wetwl.html.
"TRAMEX wet Wall Detector" http://www.yestek.com/tramex–wwd.htm.
"Moisture Meters for Wood" TRAMEX Meters for Wood, http://www.tramexltd.com/page/moistwd.html.
"Electrodes and Pin" TRAMEX Moisture Detection Equipment. http://www.tramexltd.com/page.pin.html.
"Echo2 Water Content Probes: Introduction" http://www.decagon.com/echo/.
"Echo2 Water Content Probes: Specification" http://www.decagon.com/echo/specs.html.
"Moisture Meters at ToolsToolsToolsTools.com" http://www. toolstoolstoolstools.com/m/Moisture_Meters/.

* cited by examiner

*Primary Examiner*—Charles H. Nolan, Jr.
(74) *Attorney, Agent, or Firm*—Fernandez & Associates, LLP

(57) ABSTRACT

A moisture detector is presented which uses the effects of moisture on the chemistry and electrical conductivity of drywall material. Conducting probes are installed in a drywall material and the level of electric current between the probes is monitored and correlated with the concentration of moisture in the drywall material along a path between the probes.

16 Claims, 1 Drawing Sheet

MOISTURE/MOLD DETECTOR

FIELD OF INVENTION

The invention relates to the field of moisture detection, and specifically to the detection of moisture in drywall material.

BACKGROUND OF INVENTION

The issue of mold contamination in residential and commercial buildings is quickly surpassing led-based paint and asbestos as one the real estate industry's most vexing and, potentially, costly problems. While legal claims for toxic mold contamination were virtually unheard of a few years ago, litigation relating to such contamination is dramatically on the rise throughout the country.

Virtually every mold expert is in agreement that the best way to prevent mold growth is to prevent water contamination. Within 48 hours after moisture has permeated drywall material, mold spores will begin to grow and colonize. Once water intrusion has occurred, early identification of the problem and a quick response are the only way to insure the maintenance of a healthy indoor environment. Presently, it is virtually impossible to observe the condition of the hidden surfaces of drywall, which are located within a building's wall cavities, absent an intrusion into or removal of a portion of the drywall material, or by visiting a potentially contaminated site and performing tests manually. Consequently, a need exists for a device that will continuously monitor and immediately detect (and give warning of) the intrusion of moisture into drywall and on its hidden surfaces.

SUMMARY OF INVENTION

The present invention describes an apparatus and method for detecting moisture in drywall material, using the effect of moisture on the chemistry and electrical conductivity of drywall material. Two conducting probes separated by a gap are installed in drywall material. A battery supplied voltage difference is applied between the two conducting probes. The level of electric current between the probes is monitored and correlates with the concentration of moisture in the drywall material along a path between the probes.

DETAILED DESCRIPTION OF PREFERRED EMBODIMENTS

Figure 1:
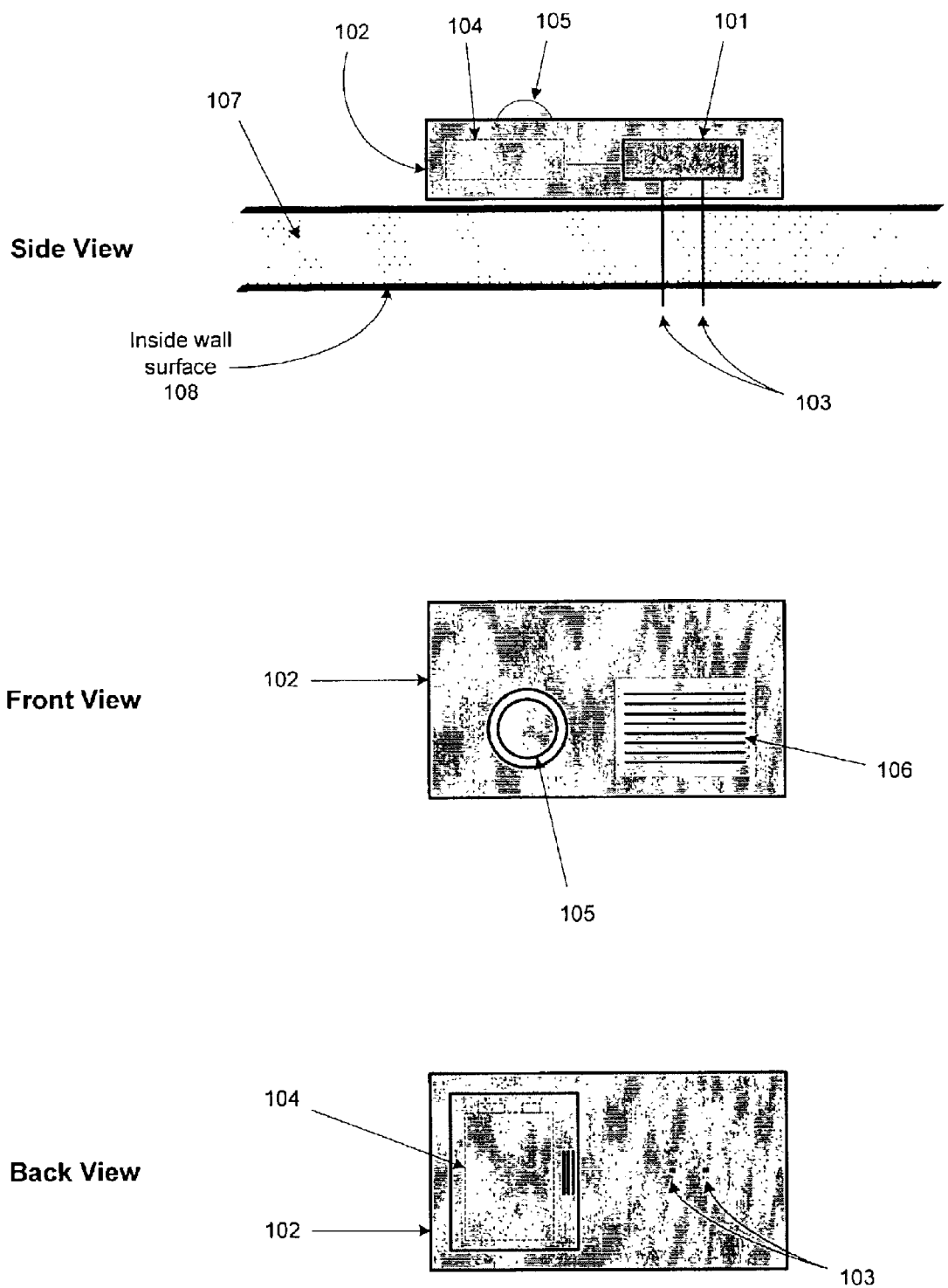
FIG. 1 is a diagram illustrating a moisture/mold detector according to a preferred embodiment of the present invention.

The invention is an electrical instrument designed specifically to monitor and detect moisture (primarily water) on the surfaces of walls inside the wall cavities of buildings, as well as within the walls themselves, for the purpose of alerting the residents or occupants therein of a potential for the growth of molds. Presently, said inside wall surfaces and wall interiors are, for the most part, impossible to observe absent an intrusion into or removal of a portion of the walls. As used herein, the term "drywall" refers to the material used in the construction of buildings, commonly known as drywall, wallboard, Sheetrock, or gypsum board (gypboard), with hydrous calcium sulphate as a main ingredient.

FIG.1 illustrates a moisture/mold detector according to a preferred embodiment of the present invention. The instrument consists of a resistive electrical system 101 housed in a small insulated container 102 that is connected to and communicating with two metal, needle-like, probes 103 protruding from one side of the container's moisture-proof exterior. The probes are connected together by electronic circuitry and are powered by a battery 104. Optimally, the circuitry is also connected to a low voltage warning light 105 or sound signal 106 (such as an intermittent beeper), or both, located on the opposite side of the instrument from the probes. However, said light and signal can also be detached from the instrument and activated on a remote basis by an electrical transmitter. The probes 103 are separated by a gap of approximately ¼ to ½ inch and run parallel to each other. The instrument is designed primarily to have the probes 103 pushed into drywall 107 so that they pass through the entire width of the wall and slightly (not more than ½ inch) protrude through the inside wall surface 108. The probes 103 can also be placed through harder materials covering the drywall 107, such as tile and wood, simply by drilling holes through such materials in order to expose the drywall surface below. (Likewise, the device can also be used to detect moisture on the non-vertical, hidden surfaces of ceilings that are constructed with drywall material. However, its novelty is its unique ability to detect moisture and dripping or flowing water on and in vertical walls.)

Once in place, the resistance of the drywall 107 material prevents an electrical connection from occurring, unless the drywall 107 material becomes moist between and around the two probes 103. Once moisture reaches a sufficient level, the chemical combination of the moisture and the drywall 107 material constitute an efficient basic conductor that effectively reduces the resistance and allows an electrical current to pass between the two probes 103. The current is then amplified and measured. When the level of electrical current reaches a designated value, the instrument triggers the warning light 105 or the sound signal 106, or both. In addition, the mere presence of surface moisture on the inside (or hidden) wall surface 108, which sufficiently flows between and around the two protruding points on the probes 103, can also provide enough conductivity to complete the electrical connection for purposes of triggering the warning light 105 or sound signal 106. The novelty of the electrical instrument is in its use of a resistance-based electrical application, which also utilizes the unique chemical composition of drywall and the change in its conductivity based on the concentration of moisture therein, to monitor moisture inside the walls of buildings and on their hidden surfaces for the specific purpose of preventing the growth of molds thereon once moisture has been detected.

Foregoing described embodiments of the invention are provided as illustrations and descriptions. They are not intended to limit the invention to precise form described. In particular, it is contemplated that functional implementation of invention described herein may be implemented equivalently in hardware, software, firmware, and/or other available functional components or building blocks. Other variations and embodiments are possible in light of above teachings, and it is thus intended that the scope of invention not be limited by this Detailed Description, but rather by Claims following.

We claim:

1. An apparatus comprising:
   a first conducting probe and a second conducting probe, the first and second conducting probes separated by a gap;
   a power supply, to provide a voltage difference between the first and second conducting probes; and a controller, to indicate when a level of electric current flowing between the first and the second conducting probes equals or exceeds a first threshold value;

wherein the first and second conducting probes are in contact with a drywall material, such that an electric current flows between the first and second conducting probes when moisture in the drywall material creates an electrical path in the drywall material between the first and second conducting probes.

2. The apparatus of claim 1, wherein the first threshold value is chosen such that a level of electric current, flowing between the first and second conducting probes and equaling or exceeding the first threshold value, indicates a concentration of moisture equaling or exceeding a second threshold value along a path in the drywall material between the first and second conducting probes.

3. The apparatus of claim 1, wherein the first threshold value is chosen such that a level of electric current, flowing between the first and second conducting probes and equaling or exceeding the first threshold value, indicates a concentration of moisture equaling or exceeding a second threshold value between and around the first and the second conducting probes.

4. The apparatus of claim 1, wherein the gap between the first and second conducting probes is between ¼ inch to ½ inch wide.

5. The apparatus of claim 1, wherein the power supply comprises a battery.

6. The apparatus of claim 1, wherein the controller causes a visual signal to be generated when a level of electric current flowing between the first and second conducting probes equals or exceeds the first threshold value, and wherein the visual signal comprises a warning light.

7. The apparatus of claim 1, wherein the controller causes a sound signal to be generated when a level of electric current flowing between the first and second conducting probes equals or exceeds the first threshold value.

8. The apparatus of claim 1, wherein the controller transmits a signal to a remote receiver when a level of electric current flowing between the first and second conducting probes equals or exceeds the first threshold value.

9. The apparatus of claim 1, further comprising a moisture-proof container, wherein the moisture proof container houses the power supply and the controller, and the first and second conducting probes protrude from the exterior of the moisture-proof container.

10. A method for detecting moisture in a drywall material comprising:

installing a first conducting probe and a second conducting probe in contact with the drywall material, the first and second conducting probes separated by a gap, wherein an electric current flows between the first and second conducting probes when moisture in the drywall material creates an electrical path between the first and second conducting probes, and choosing a first threshold value such that a level of electric current, flowing between the first and second conducting probes and equaling or exceeding the first threshold value, indicates a concentration of moisture equaling or exceeding a second threshold value along a path in the drywall material between the first and second conducting probes.

11. The method of claim 10, further comprising monitoring a concentration of moisture in the drywall material for the purpose of alerting building owners of the potential for the growth of molds in and on the drywall material.

12. The method of claim 10, further comprising monitoring a concentration of moisture in the drywall material for the purpose of alerting building occupants of the potential for the growth of molds in and on the drywall material.

13. The method of claim 10, further comprising monitoring a concentration of moisture in the drywall material, and alerting building owners of the potential for the growth of molds in and on the drywall material when the level of electric current flowing between the first and second conducting probes equals or exceeds the first threshold value.

14. The method of claim 10, further comprising monitoring a concentration of moisture in the drywall material, and alerting building occupants of the potential for the growth of molds in and on the drywall material when the level of electric current flowing between the first and second conducting probes equals or exceeds the first threshold value.

15. A method of making an apparatus for detecting moisture in a drywall material, the method comprising:

providing a first conducting probe and a second conducting probe, connecting a power supply to provide a voltage difference between the first and second conducting probes, coupling a controller to the first and second conducting probes, setting the to controller indicate when a level of electric current flowing between the first and second conducting probes equals or exceeds a first threshold value, the first threshold value being chosen to correlate with a concentration of moisture equaling or exceeding a second threshold value along a path in the drywall material between the first and second conducting probes.

16. The method of claim 15, wherein the controller indicates by at least one signal selected from the group consisting of a visual signal, a sound signal, and a signal transmitted to a remote receiver.

* * * * *